United States Patent

Voit et al.

[11] Patent Number: 5,679,855
[45] Date of Patent: Oct. 21, 1997

[54] PREPARATION OF BENZOPHENONE IMINES

[75] Inventors: Guido Voit, Schriesheim; Martin Holderbaum; Tom Witzel, both of Ludwigshafen; Alexander Aumüller, Neustadt, all of Germany

[73] Assignee: BASF Aktiengesellschaft, Ludwigshafen, Germany

[21] Appl. No.: 561,300

[22] Filed: Nov. 21, 1995

[30] Foreign Application Priority Data

Nov. 26, 1994 [DE] Germany ............... 44 42 138.9

[51] Int. Cl.⁶ ........................... C07C 249/02
[52] U.S. Cl. ............................. 564/269
[58] Field of Search ........................ 564/269

[56] References Cited

U.S. PATENT DOCUMENTS

| | | | |
|---|---|---|---|
| 2,533,723 | 7/1950 | Dombrow | 260/566 |
| 4,083,869 | 4/1978 | Isshiki et al. | 260/566 R |
| 4,130,586 | 12/1978 | Isshiki et al. | 260/566 R |

FOREIGN PATENT DOCUMENTS

| | | |
|---|---|---|
| 030563 | 7/1984 | Japan . |
| 1280551 | 7/1972 | United Kingdom . |

OTHER PUBLICATIONS

Verardo et al, Synthetic Communications, vol. 18 (1988), pp. 1501–1511.
Hayashi et al, Nippon Kagaku Kaishi (1973), pp. 1392–1396.
Mignonac, Comp. Rend., vol. 169, (1919), pp. 237–239.
Hayashi et al, Nippon Kagaku Kaishi (1974), p. 2216–2218.
Hayashi et al, Chemistry Letters (1976), pp. 205–206.

*Primary Examiner*—Peter O'Sullivan
*Attorney, Agent, or Firm*—John H. Shurtleff

[57] ABSTRACT

A process for preparing benzophenone imines of the general formula I

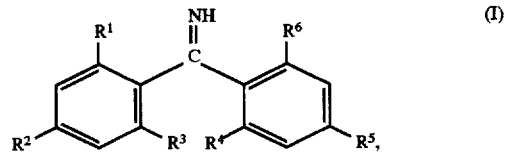

where $R^1$ to $R^6$ are hydrogen, $C_1$-to $C_4$-alkoxy, $C_1$-to $C_2$-alkylamine or $C_2$-to $C_4$-dialkylamine, by reacting benzophenones of the general formula II

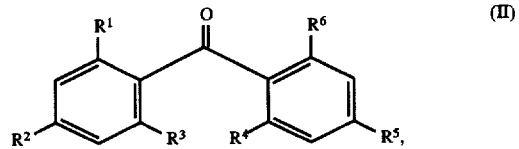

where $R^1$ to $R^6$ have the abovementioned meanings, in liquid ammonia in the presence of oxides of the elements boron, aluminum, gallium, indium, silicon, germanium, tin, lead, phosphorus, arsenic, antimony, bismuth, scandium, yttrium, titanium, zirconium, vanadium, niobium, tantalum or mixtures thereof at from 50° to 150° C. and from 50 to 350 bar is described.

14 Claims, No Drawings

PREPARATION OF BENZOPHENONE IMINES

The present invention relates to a process for preparing benzophenone imines from benzophenones in liquid ammonia.

In the direct reaction of benzophenone in molten form or in solution with gaseous or liquid ammonia, iron (III) chloride (JP-A-61/030563, yield: 57%), organic acids such as benzoic acid (U.S. Pat.No. 4,130,586, yields: 18–65%) or ammonium chloride (Synthetic Communications 18 (1988), 1501–1511; yield 94%) must be added as a catalyst. The disadvantages of these processes are the yields, which are low in some cases, but in particular a complicated removal of the catalyst or a forced accumulation of salt.

Under drastic conditions (400° C.), benzophenone can be reacted in the gas phase with heterogeneous catalysis on thorium oxide [Nippon Kagaku Kaishi (1973), 1392–1396 or Compt. Rend. 169 (1919), 237–239] or thorium oxide/silicon oxide [Nippon Kagaku Kaishi (1974), 2216–2218]. A disadvantage of this process is the complicated technique (high temperature, high vacuum) and a high proportion of decomposition products.

The heterogeneously catalyzed reaction of benzophenone in the liquid phase with gaseous ammonia on ion exchangers is known from Chemistry Letters (1976), 205–206. The yields of 10%, however, are unsatisfactorily low.

U.S. Pat. No. 4,083,869 discloses a process for preparing benzophenone imine in which benzophenone is reacted in the liquid phase, preferably in an organic solvent, with gaseous or supercritical ammonia on oxides of metals of the 2nd to 5th period of groups III to V, such as titanium oxide or aluminum oxide, at from 150° to 250° C. and from 1 to 50 bar. The yields of at most 60%, however, are unsatisfactory.

It is an object of the present invention to remedy the abovementioned disadvantages.

We have found that this object is achieved by a process for preparing benzophenone imines of the general formula I

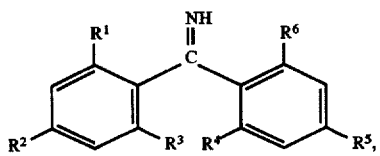

where $R^1$ to $R^6$ are hydrogen, $C_1$- to $C_4$-alkoxy, $C_1$- to $C_2$-alkylamine or $C_2$- to $C_4$-dialkylamine, which comprises reacting benzophenones of the general formula II

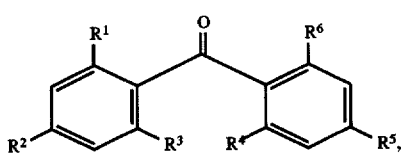

where $R^1$ to $R^6$ have the abovementioned meanings, in liquid ammonia in the presence of oxides of the elements boron, aluminum, gallium, indium, silicon, germanium, tin, lead, phosphorus, arsenic, antimony, bismuth, scandium, yttrium, titanium, zirconium, vanadium, niobium, tantalum or mixtures thereof at from 50° to 150° C. and from 50 to 350 bar.

The process according to the invention is carried out as follows:

The process can be carried out either batchwise in stirred autoclaves or continuously in a tubular reactor, preferably continuously in a tubular reactor, at from 50° to 150° C., preferably from 80° to 140° C., particularly preferably from 120° to 140° C. and from 50 to 350 bar, preferably from 150 to 250 bar, particularly preferably from 180 to 220 bar.

Suitable catalysts are oxides or mixed oxides of the elements boron, aluminum, gallium, indium, silicon, germanium, tin, lead, phosphorus, arsenic, antimony, bismuth, scandium, yttrium, titanium, zironium, vanadium, niobium and tantalum, preferably oxides or mixed oxides of the elements boron, aluminum, gallium, silicon, tin, lead, antimony, bismuth, titanium, zironium, vanadium and niobium, particularly preferably oxides or mixed oxides of the elements aluminum, silicon, titanium, zirconium and vanadium, in particular titanium oxides.

The catalysts can be employed in the form of powder (stirred autoclave) or in the form of tablets or extrudates (tubular reactor).

Separation of the water of reaction during or after the reaction is unnecessary.

In the continuous procedure, as a rule the loading is adjusted to be from 0.1 to 0.6 kg of benzophenone per liter of catalyst per hour, preferably from 0.2 to 0.4 kg/l/h.

Benzophenone can be employed in molten form or in solution, preferably in molten form.

The ammonia is employed in liquid form. Preferably, from 1 to 10 kg of ammonia are employed per kg of benzophenone, particularly preferably from 3 to 6 kg/kg.

Benzophenone imine is used as an intermediate in the preparation of light screens (eg. ethyl 2-cyano-3,3-diphenylacrylate) [Bull. Chem. Soc. Ft. (1963) 1576–1583].

The substituents $R^1$ to $R^6$ in the compounds I and II have the following meanings:

$R^1$, $R^2$, $R^3$, $R^4$, $R^5$ and $R^6$ independently of one another are hydrogen, $C_1$- to $C_4$-alkoxy such as methoxy, ethoxy, n-propoxy, isopropoxy, n-butoxy, isobutoxy, sec-butoxy and tert-butoxy, preferably methoxy, ethoxy, n-propoxy and n-butoxy, particularly preferably methoxy and ethoxy, $C_1$- to $C_2$-alkylamine such as methylamine and ethylamine, preferably methylamine, $C_2$- to $C_4$-dialkylamine such as dimethylamine and diethylamine, preferably dimethylamine.

The compound where $R^1$ to $R^6$ are hydrogen is particularly preferred.

EXAMPLES

Example 1

In a 250 ml stirred autoclave, 15 g of benzophenone in 125 ml of ammonia together with 2 g of titanium oxide powder were stirred for 5 h at 200 bar and 130° C. After distilling off the ammonia and removing the catalyst, the two-phase mixture discharged was homogenized with dimethylformamide and investigated by means of GC:

Conversion: 95%

Selectivity: 99%

Example 2

180 g of benzophenone/h and 720 g of ammonia/h were passed through a tubular reactor, packed with 300 ml of titanium oxide (3 mm extrudates), at 200 bar and 130° C. After distilling off the ammonia, the two-phase mixture discharged was homogenized with dimethylformamide and investigated by means of GC:

Conversion: 95%

Selectivity: 99%

Example 3

60 g of benzophenone/h and 720 g of ammonia/h were passed through a tubular reactor, packed with 300 ml of titanium oxide (3 mm extrudates), at 200 bar and 130° C. After distilling off the ammonia, the two-phase mixture discharged was homogenized with dimethylformamide and investigated by means of GC:

Conversion: 98%
Selectivity: 99%

Example 4

24 g per hour of a 25% strength methanolic benzophenone solution and 36 g of ammonia were passed through a tubular reactor, packed with 60 ml of titanium oxide (3 mm extrudates), at 120 bar and 130° C. After distilling off the ammonia, the mixture discharged was investigated by means of GC:

Conversion: 91%
Selectivity: 99%

EXAMPLE 5

24 g per hour of a 25% strength methanolic benzophenone solution and 36 g of ammonia were passed through a tubular reactor, packed with 60 ml of aluminum oxide (3 mm extrudates), at 120 bar and 130° C. After distilling off the ammonia, the mixture discharged was investigated by means of GC:

Conversion: 58%.
Selectivity: 99%

We claim:

1. A process for preparing benzophenone imines of the general formula I

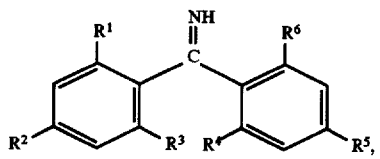

where $R^1$ to $R^6$ are hydrogen, $C_1$- to $C_4$-alkoxy, $C_1$- to $C_2$-alkylamine or $C_2$- to $C_4$-dialkylamine, which comprises reacting benzophenones of the general formula II

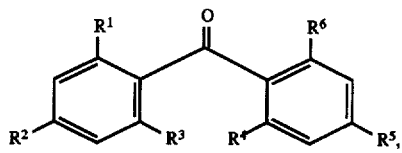

where $R^1$ to $R^6$ have the abovementioned meanings, in liquid ammonia in the presence of oxides of the elements boron, aluminum, gallium, indium, silicon, germanium, tin, lead, phosphorus, arsenic, antimony, bismuth, scandium, yttrium, titanium, zirconium, vanadium, niobium, tantalum or mixtures thereof at from 50° to 150° C. and from 50 to 350 bar.

2. A process for preparing benzophenone imines as claimed in claim 1, wherein $R^1$ to $R^6$ are hydrogen.

3. A process for preparing benzophenone imines as claimed in claim 1, wherein the oxides empoloyed are those of the elements boron, aluminum, gallium, silicon, tin, lead, antimony, bismuth, titanium, zironium, vanadium, niobium or mixtures thereof.

4. A process for preparing benzophenone imines as claimed in claim 1, wherein the oxides employed are those of the elements aluminum, silicon, titanium, zirconium, vanadium or mixtures thereof.

5. A process for preparing benzophenone imines as claimed in claim 1, wherein the oxides employed are titanium oxides.

6. A process for preparing benzophenone imines as claimed in claim 1, wherein the reaction is carried out at from 80° to 140° C. and from 150 to 250 bar.

7. A process for preparing benzophenone imines as claimed in claim 1, wherein the reaction is carried out at from 120° to 140° C. and from 180 to 220 bar.

8. A process as claimed in claim 1, wherein the benzophenone II is reacted in the molten state and in the absence of a solvent at a temperature of from 80° to 140° C. with liquid ammonia under a pressure of more than 150 bar.

9. A process as claimed in claim 8, wherein the catalyst is titanium dioxide.

10. A process as claimed in claim 8, wherein the reaction is carried out continuously by conducting the liquid reactants through a fixed bed of the catalyst and the ammonia is separated by distillation from the reaction product.

11. A process as claimed in claim 10, wherein the catalyst is titanium dioxide.

12. A process as claimed in claim 11, wherein molten benzophenone is reacted with the liquid ammonia.

13. A process as claimed in claim 1, wherein the substituents $R^1$ to $R^6$ of the benzophenone II, independently of each other, are selected from the group consisting of hydrogen, methoxy, ethoxy, methylamine, ethylamine, dimethylamine and diethylamine.

14. A process as claimed in claim 1, wherein molten benzophenone is reacted with the liquid ammonia at a temperature of from 120° to 140° C. and under a pressure of from 120 to 220 bar.

* * * * *